United States Patent [19]

Schluter et al.

[11] 4,219,334
[45] Aug. 26, 1980

[54] POLYMER CARRIER AND METHOD FOR CARRYING OUT SCIENTIFIC, ANALYTICAL AND DIAGNOSTIC EXAMINATIONS

[75] Inventors: Gert Schluter, Liederbach; Wilhelm Schuster, Frankfurt am Main, both of Fed. Rep. of Germany

[73] Assignee: Battelle-Institut e. V., Postfach, Fed. Rep. of Germany

[21] Appl. No.: 883,190

[22] Filed: Mar. 3, 1978

[30] Foreign Application Priority Data

May 3, 1977 [DE] Fed. Rep. of Germany ....... 2709625

[51] Int. Cl.² ............... G01N 33/16; G01N 21/02; G01N 31/14
[52] U.S. Cl. .................. 23/230 B; 252/408; 422/56; 424/3; 424/8; 435/4
[58] Field of Search ............ 23/230 B, 253 TP; 252/408; 422/56; 424/3, 8

[56] References Cited

U.S. PATENT DOCUMENTS

| | | | |
|---|---|---|---|
| 3,963,442 | 6/1976 | Bullard | 23/253 TP |
| 4,038,485 | 7/1977 | Johnston | 23/230 B |

OTHER PUBLICATIONS

Chemical Abstracts, 85:119234z (1976).
L. Hallman, "Klinische Chemie und Mikrosokopie," Thieme-Verlag (1966).
Wittekind et al., Blut. vol. 32, pp. 70–78 (1976).

*Primary Examiner*—Sidney Marantz
*Attorney, Agent, or Firm*—Fisher, Christen & Sabol

[57] ABSTRACT

A polymer carrier for scientific, analytical or diagnostic examinations. The carrier consists of a soluble polymer in which the materials to be examined and/or required for examinations are incorporated and which is fully dissolved for complete release of said materials.

23 Claims, No Drawings

POLYMER CARRIER AND METHOD FOR CARRYING OUT SCIENTIFIC, ANALYTICAL AND DIAGNOSTIC EXAMINATIONS

BACKGROUND OF THIS INVENTION

1. Field of the Invention

This invention relates to a polymer carrier and a method for carrying out scientific, analytical and diagnostic examinations. In particular, this invention relates to a polymer carrier for the rapid detection of pathogenic germs, pathological cell forms and other pathological processes in the human or animal organism.

2. Prior Art

In general and especially in medical laboratory investigations, staining methods are used for the microscopic diagnosis of cells from tissue samples and for the detection of microorganisms. For this purpose, the specimens often must be subjected to very time- and material-consuming reactions, depending on the required degree of differentiation of the intracellular structures and substances to be prepared. For the staining procedure, the necessary stains are dissolved, and the microscopic slides with the sample material to be stained are either immersed in these solutions or coated with the staining solution. The entire staining process often includes several steps of intermediate treatments in different baths. The staining of the sample materials is influenced by various factors, e.g., the type of stain, the reaction time, the pH-value and impurities or precipitates in the staining solution. Many staining solutions tend to precipitate, especially in dilute solution.

The Giemsa solution [e.g., according to L. Hallmann, "Klinische Chemie and Mikrosokopie", Thieme-Verlag (1966)], which is most frequently used in haematology for blood cell examination and detection of pathogenic germs in blood, e.g., trypanosomes or malaria parasites, is very unstable. Such staining solution must be prepared fresh from a parent solution immediately before it is used and must be carefully filtered before the staining process.

Another stain taken into consideration in the examinations underlying this invention is the modified Pappenheim staining method with the purified stains azure B and eosin G, which is recommended especially for staining blood and bone-marrow smears [Wittekind et al., Blut Vol. 32, pp. 70 to 78 (1976)]. Because of the purified stains, such staining method is said to meet the requirements of adequate cell representation better than other panoptic staining methods as, for example, "Giemsa-May-Grunwald". In conventional applications, however, such staining method also has the drawback that the necessary stains must always be prepared fresh immediately before use (the unused excess material being discarded). Furthermore, the staining mixture must be diluted with a buffer solution (pH 6.5) on the specimen to be stained and rinsed off with distilled water after the staining process.

Besides the staining methods described above, others used for diagnostic purposes and scientific examinations also have the drawback that they are time-consuming and complicated. They require constant renewal of the reagents and cannot be standardized in terms of their effect of the specimen.

There are additional methods besides the Giemsa staining method that can be used for the detection of pathogenic germs, e.g., trypanosomes in the blood. With the immunofluorescent method, the germs are specifically identified by means of fluorescent antibodies. A direct and indirect method can be used in immunofluorescent staining. In the direct method the antibody is conjugated with FITC (fluorescein isothiocyanate). Together with the antigen it forms an FITC-antibody-antigen complex. In the indirect method, a fluorochrome-labelled antibody is used which combines with the antigen-antibody complex.

The staining solutions required for the two latter processes, with the antibodies contained in them, also keep only for a limited period of time. They must always be stored in a freezer. Such methods furthermore require great precision in order to ensure the necessary even coating of the specimen with the staining solution.

Not only the staining reactions in medical laboratory examinations, but also other microscopic detection reactions, e.g., in criminology, require complicated time-consuming methods and the use of extreme care.

One method frequently used to detect organic diseases is the determination of chemical substances in body fluids. For example, to determine lactate dehydrogenase (LDH) in serum in the case of blood or liver diseases or cardiac infraction, reagents are added to the sample of body fluid and the resulting changes are determined photometrically. Such determination is based on the principle that the lactate dehydrogenase enzyme catalyzes the hydrogen transfer reaction:

$$\text{pyruvate} + \text{NADH} + \text{H}^+ \rightleftharpoons \text{lactate} + \text{NAD}^+$$

wherein the equilibrium is shifted to the side of the lactate and NAD (nioctinamide-adenine dinucleotide). The LDH activity is determined from the rate of decrease of NADH (reduced nioctinamide-adenine dinucleotide) caused by such reaction. NADH can be easily determined because of its absorption at 366, 340 or 334 nm.

Implementation of such methods involves mixing and pipetting processes that require extreme accuracy and are rather time-consuming. In addition, some of the reagents have to be prepared fresh from a parent solution before use. The reactions are furthermore influenced by a number of factors, e.g., the effects of the reagents, impurities, etc.

BROAD DESCRIPTION OF THIS INVENTION

An objective of this invention is to overcome the above-described drawbacks of the prior art and develop a method by which scientific, analytical or diagnostic examinations can be performed fast, easily and reliably. Other objects and advantages of this invention are set forth herein or are obvious herefrom to one ordinarily skilled in the art. The objects and advantages of this invention are achieved by the carrier and method of this invention.

It has been found that the above-described objective of this invention can be achieved in a technically advanced manner if in accordance with this invention a carrier is used that consists of a soluble polymer in which the materials to be examined and/or required for the examination are incorporated. These materials are partly or completely released when the carrier is superficially or entirely dissolved.

The process according to this invention is characterized in that a soluble polymer carrier is used in which the materials to be examined and/or required for the examination are incorporated, and in that this polymer carrier is dissolved immediately before the examination.

If in the process according to this invention a polymer carrier is used in which only the materials to be examined are incorporated or arranged, the carrier is dissolved in a suitable solvent immediately before the examination. According to an especially advantageous embodiment of this invention, it is possible to examine a specimen, e.g., cell material, at any later point in time. For this purpose a film containing appropriate stains is dissolved superficially on one side, brought into contact with the surface from which the cells are to be taken and removed again. The cells are then on the adhesive surface of the film and can be fixated by dipping the film briefly into a fixing solution, e.g., ethanol, that does not dissolve the film. The film is then pressed with its adhesive side onto a microscopic slide so that all fixated (fixed) cells are enclosed between the film and microscopic slide. The microscopic slide with the cells can then be mailed, stored or otherwise kept, and examined at a later time after dissolution of the film in water (which results in staining of the cells). Instead of the microscopic slide, a second soluble film can be used for enclosing the cells. In this case it may be useful for the later examinations to dissolve all the polymer material and separate the cells from the solution by centrifuging. The polymer films used are preferably transparent so that the cells material enclosed in them can also be examined directly by microscope. In these embodiments the cells lie in one optical plane.

The carriers in which the cells are incorporated may also contain the reagents necessary for performing examinations. If the carrier contains only the materials required for performing examinations (e.g., stains and immunofluorescent reagents or enzyme substrates), but not materials to be examined, the carrier is wetted on one side with a suitable solvent. This side of the carrier is then brought into contact with the material to be examined, and the carrier is subsequently dissolved in the solvent immediately before the examination.

It has been found that the incorporation of cells from the human or animal organism in water-soluble films is especially suited for didactic purposes.

In the process according to this invention, suspended and fixated cell material, e.g., from the vaginal epithelium or any other organ, is stirred into and homogeneously distributed in the still liquid polymer carrier. This solution is processed into a 0.1 mm-thick film in which the cells are incorporated. The cell materials is incorporated in the film in such a way that a quantitative cell count in separate segments of defined size can be performed. With this method it is also possible to separate the cell material from the polymer carrier by dissolving the polymer carrier, e.g., in water.

Thus, it is possible to provide a large number of persons, e.g., in medical or biological university or high-school classes, with sufficient and representative amounts of the same original method. With this well-preserved material, students can study the cellular structure or organs and learn to recognise pathological changes by micromorphological characteristics. In addition, staining techniques can be learned and tested with cell material preserved by this method.

For examinations of body fluids with respect to diseases in the animal or human organism, in which the body fluid is mixed with reagents and the reaction products are analyzed in a conventional manner, a polymer body is added to the proper amount of sample fluid. The polymer body is soluble in this sample fluid. The reagents required for the examination are incorporated in the polymer body in accurately dosed quantities. For this purpose, the polymer body preferably contains enzyme substrates, enzymes, enzyme substrate/enzyme/immune reagent mixtures and buffer salts.

The soluble polymer carrier covered by this invention preferably consists of polyvinyl alcohol or polyvinyl pyrrolidone. Particularly suitable is a vinyl pyrrolidone polymer having a molecular weight between about 40,000 and 700,000, and which is made from mixed polymers of vinyl pyrrolidone and vinyl acetate with differing vinyl acetate concentrations. Also particularly suitable is a soluble polymer carrier made from a partially saponified low-polymer-weight polyvinyl alcohol. These polymers may contain plasticizers, e.g., glycerol.

Suitable agents for dissolving the polymer carrier are solvents or mixtures of solvents which have no detrimental effects on the materials to be examined and which do not influence the reaction to be carried out. Preference is given to a carrier which is soluble in water. Other suitable solvents and mixtures of these solvents with water, e.g., alcohol/water or acetone/water mixtures, can be used as well. The mixture proportions of the solvent components can be adjusted to the solubility of the polymer used and/or to the type of reaction to be carried out.

To stain cells, tissue sections and micro-organisms, it is possible to incorporate conventional stains, immunofluorescent reagents or enzyme substrates into the polymer carriers. To perform reactions in solution, the carriers are provided with enzyme substrates, enzymes or immune reagents.

The polymer carriers covered by this invention are prepared by introducing the substances required for the specific reactions into the polymer solution. From this polymer solution a film or body is subsequently formed. Films, e.g., 0.1 mm in thickness, can be obtained by spreading polymer solutions on a substrate, e.g., glass or polyethylene film. Thus, the reagents are coated with the polymer and enclosed in durable form.

The polymer carrier may also be prepared in other forms suitable for storage or dosage, e.g., in the form of beads or spheres. The reagent-containing polymer carrier may, for example, also be applied to a spatula which is then used for stirring the reaction solution. Polymer films with homogeneous distributed reagents and cells may also be perforated to achieve a better solubility.

The type and quantity of the reagents and their distribution in the polymer body or film to be prepared can be exactly predetermined and adjusted to the later requirements by adequate dosage and homogenization in the solution.

By way of summary, this invention includes a polymer carrier for scientific, analytical or diagnostic examinations. The carrier consists of a soluble polymer in which the materials to be examined and/or required for examinations are incorporated and which is superficially or fully dissolved for partial or complete release of said materials. The soluble polymer can be, for example, a polyvinyl alcohol or polyvinyl pyrrolidone. The polymer can be soluble in water and/or alcohol. The carrier can contain chemical or biological reagents, stains, immunofluorescent reagents, enzyme substrates, enzymes, enzyme substrate/enzyme/immuno reagent mixtures and/or buffer salts in homogeneous distribution. The carrier can contain microorganisms, cells, particles or the like in homogeneous distribution. The carrier can be in the form of a film or a foil. The carrier can also consist of at least two layers of film between which the materials to be examined, e.g., cells, are arranged.

This invention also includes a method for scientific, analytical or diagnostic examinations. A soluble polymer carrier is used in which the materials to be examined and/or required for examinations are incorporated. The polymer carrier is dissolved immediately before the examination. A soluble polymer carrier can be used in which the materials required for examinations are incorporated. The carrier is wetted on one side with a suitable solvent, brought into contact on this side with the material to be examined, and subsequently dissolved in the solvent immediately before the examination. The carrier can be wetted with or dissolved in water and/or alcohol. A polymer carrier is used which is soluble in body fluids to be examined and in which the reagents required for examinations are incorporated in accurately dosed quantities. The carrier is dissolved in the proper amount of sample fluid and the reaction products are determined in a conventional manner.

DETAILED DESCRIPTION OF THIS INVENTION

As used herein, all parts, ratios and percentages are on a weight basis unless otherwise stated therein or otherwise obvious to one ordinarily skilled in the art.

EXAMPLE 1

A mixture of 300 parts by weight of polyvinyl alcohol (88 mole percent of hydroxyl groups; visosity of 4 c.p. according to DIN 53015), 150 parts by weight of Giemsa solution, 120 parts by weight of glycerol p.a. and 430 parts by weight of distilled water is homogenized. This solution is then cast into a 0.1 mm-thick layer which, after evaporation of the water, forms a polymer film in which the Giemsa stain particles are absolutely uniformly distributed. The polymer film is brought into contact with the surface of a microscopic slide which is covered, e.g., with blood cells. The lying slide with the polymer film on its upper surface is then covered with water. After dissolution of the film, the stain is released and the blood cells are stained. The entire process only takes a few minutes. The staining is absolutely uniform and in every respect meets the requirements of cell representation.

EXAMPLE 2

500 parts by weight of purified azure B, 50 parts by weight of purified eosin, 300 parts by weight of polyvinyl alcohol (88 mole percent of hydroxyl groups; viscosity of 4 c.p. according to DIN 53015), 120 parts by weight of glycerol p.a. and 580 parts by weight of water are mixed. Staining and examination are then carried out as described in Example 1.

EXAMPLE 3

A mixture of 175 parts by weight of polyvinyl alcohol (88 mole percent of hydroxyl groups; viscosity of 4 c.p. according to DIN 53015), 140 parts by weight of glycerol p.a., 255 parts by weight of distilled water, and 500 parts by weight of Wright's stain is homogenized. The examination is carried out as described in Example 1.

EXAMPLE 4

For determining trypanosomes, 240 parts by weight of a fluorescent antibody solution are added to 750 parts by weight of a polymer solution which consists of (i) 280 parts by weight of polyvinyl alcohol, 70 parts by weight of sorbite powder and 650 parts by weight of distilled water, or (ii) 300 parts by weight of polyvinyl alcohol, 120 parts by weight of glycerol p.a., 400 parts by weight of ethyl alcohol p.a. and 440 parts by weight of distilled water. Thereupon a film or body is formed. Using the method described in Example 1, the film is superficially dissolved on one side and brought into contact with the surface of a microscopic slide which carries the smear to be examined.

If the direct detection method is used, the polymer film on the microscopic slide is covered with a conjugated buffer and incubated at 37° C. in a humidified chamber for about 1 hour. The sample is then rinsed off, dried and examined under the fluorescence microscope.

When using the indirect method, the process applied is the same as described above. However, fluorescence is achieved through incubation with a second FITC-conjugated antibody against the first antibody which is not fluorescent.

EXAMPLE 5

Adequate quantities of the reagents required for LDH determination in serum, e.g., $Na_2HPO_4/NaH_2PO_4$/sodium pyrovate/NADH, are added to a polymer solution and homogenized. The following polymer solutions are used:

(I)
- 300 parts by weight of polyvinyl alcohol (88 mole percent of hydroxyl groups; viscosity of 4 c.p. according to DIN 53015)
- 120 parts by weight of glycerol p.a.
- 400 parts by weight of ethyl alcohol p.a.
- 400 parts by weight of distilled water (II)
- 280 parts by weight of polyvinyl alcohol (88 mole percent of hydroxyl groups; viscosity of 4 c.p. according to DIN 53015)
- 70 parts by weight of sorbite powder
- 650 parts by weight of distilled water These polymer solutions with the required reagents are used to make films, each square centimeter of film containing 21.6 mg of $Na_2HPO_4.2H_2O$, 27.8 mg of $NaH_2PO_4.2H_2O$, 0.2 mg of sodium pyruvate and 35.8 mg of NADH. 3 ml of distilled water is transferred into a cuvette with a pipette and stirred for 5 to 10 seconds together with the above-indicated quantities of buffer/pyruvate and NADH after the film has been added. Thereupon 0.1 ml of fresh non-haemolysing serum is added by pipetting and mixed with the solution. Extinction is measured after 1, 2 and 3 minutes at 366, 340 and 334 nm, using a conventional photometer. The enzyme content mU/ml is derived from the measured extinction difference per minute.

EXAMPLE 6

The cells of a vaginal smear suspended in alcohol (50 percent) are mixed with the constituents of the polymer carrier as follows:

7.2 gm of alcoholic cell suspension (ethyl solution) is mixed with 100 parts by weight of a polymer solution consisting of 30 parts by weight of polyvinyl alcohol, 12 parts by weight of glycerol p.a. and 58 parts by weight of distilled water.

This mixture is used for making a film having a 0.1 mm thickness. A film segment of 160×200 mm contains a total of about $3 \times 10^6$ uniformly distributed cells.

EXAMPLE 7

1 to 10 percent by weight p-nitrophenyldiazonium-p-toluosulfonate is dissolved in a solution of 30 percent by weight polyvinylalcohol with low molecular weight in 12 gm. of glycerine p.a. and 58 gm. of distilled water. The solution is degassed and a pasty mass is obtained. From this solution a film having a thickness of 0.2 mm (dry) is formed and dried at the ambient temperature under 300 mbar pressure.

For coupling with bilirubin (similar to the method of Kijmans and van den Bergh), chips of the film are dissolved in a urine sample. In the presence of bilirubin the urine sample becomes blue-violet. The staining can be quantitatively measured by UV-photometry by comparison with a standard curve.

EXAMPLE 8

A diazonium salt solution, prepared by the method described in Example 7, is added by means of a pipette into dioxane agitated with a high-speed-stirrer. After precipitation of an adsorbed substance consisting of polyvinylalcohol and diazonium salt, dioxane is decanted off. The precipitation is washed with dioxane and dried as in Example 7. A small amount of the precipitation is added to the urine sample for coupling it with bilirubin. In the presence of bilirubin the sample becomes blue-violet. The quantitative evaluation of the staining can be carried out as described in Example 7.

What is claimed is:

1. A process for preparing a product for scientific, analytical or diagnostic examination which comprises the steps:
   (a) admixing a material to be examined and/or a substance required for the examination with a solution comprised of a soluble carrier and a solvent for the carrier, and
   (b) evaporating off the solvent, the material and/or substance being uniformly dispersed in the soluble carrier, and said product being formed,
said product comprising the material and/or substance and the soluble carrier, the soluble carrier consisting of a soluble polymer, the material to be examined and/or the substance required for the examination being uniformly dispersed and hermetically sealed without exposure to air in the soluble carrier being capable of fully dissolving in a solvent for the carrier, whereby there is a complete release of the material and/or substance.

2. The product prepared by the process of claim 1.

3. A product as claimed in claim 2 wherein the soluble polymer is soluble in water and/or ethanol.

4. A product as claimed in claim 2 wherein the soluble polymer is selected from the group polyvinyl alcohol and polyvinyl pyrrolidone.

5. A product as claimed in claim 2 wherein the polymer is soluble in water and/or ethanol.

6. A product as claimed in claim 2 wherein the substance is a chemical or biological, reagent, a stain, an immunofluorescent reagent, an enzyme substrate/enzyme/immuno reagent mixture and/or a buffer salt.

7. A product as claimed in claim 6 wherein the material is microorganisms or cells.

8. A product as claimed in claim 7 wherein the carrier is in the form of a film or foil.

9. A product as claimed in claim 8 wherein the carrier is in the form of at least two sandwiched layers.

10. A product as claimed in claim 9 wherein the material is cells.

11. A product as claimed in claim 2 wherein the substance is a chemical or biological reagent, a stain, an immunofluorescent reagent, an enzyme substrate, an enzyme, an enzyme substrate/enzyme/immuno reagent mixture and/or a buffer salt.

12. A product as claimed in claim 2 wherein the material is microorganisms or cells.

13. A product as claimed in claim 2 wherein the carrier is in the form of a film or foil.

14. A product as claimed in claim 2 wherein the carrier is in the form of at least two sandwiched layers.

15. A product as claimed in claim 14 wherein the material is cells.

16. A product as claimed in claim 2 wherein the evaporation is achieved at room temperature.

17. A as claimed in claim 2 where the solvent used in step (a) is water and/or ethanol.

18. A method for scientific, analytical or diagnostic examinations which comprises contacting the product of claim 2 with a solvent, whereby the polymer carrier in such product is dissolved in such solvent fully releasing the homogeneously dispersed material and/or substance into such solvent immediately before examination, a solution being formed, and using such solution for a scientific analytical or diagnostic examination.

19. A method as claimed in claim 18 wherein the carrier is dissolved in water and/or ethanol.

20. A method as claimed in claim 18 wherein the polymer carrier is soluble in the body fluids to be examined and the substance required for the examination are reactive with the body fluids and are incorporated in the carrier in accurately dosed quantities, and the carrier is dissolved in a suitable amount of sample body fluid and the reaction products are determined.

21. A method as claimed in claim 18, wherein the substance required for the examination has been incorporated into the soluble polymer carrier, the product is wetted on one side with a suitable solvent, the wetted side of the product is brought into contact with a material to be examined, and the product is subsequently fully dissolved in a solvent immediately before examination.

22. A method as claimed in claim 21 wherein the side of the product is wetted with water and/or ethanol.

23. A method as claimd in claim 21 wherein the product is subsequently fully dissolved in water and/or ethanol.

* * * * *